(12) United States Patent
Maksym et al.

(10) Patent No.: US 9,663,798 B2
(45) Date of Patent: May 30, 2017

(54) EXPRESSION METHOD

(75) Inventors: Lukas Maksym, Cologne (DE); Ramona Knab, Neuss (DE); Stefan Evers, Mettmann (DE); Karl-Heinz Maurer, Erkrath (DE); Johannes Bongaerts, Dormagen (DE)

(73) Assignee: BASF SE, Ludwigshafen (DE)

( * ) Notice: Subject to any disclaimer, the term of this patent is extended or adjusted under 35 U.S.C. 154(b) by 355 days.

(21) Appl. No.: 14/110,724

(22) PCT Filed: Apr. 5, 2012

(86) PCT No.: PCT/EP2012/056262
§ 371 (c)(1),
(2), (4) Date: Apr. 8, 2014

(87) PCT Pub. No.: WO2012/139964
PCT Pub. Date: Oct. 18, 2012

(65) Prior Publication Data
US 2014/0220628 A1   Aug. 7, 2014

(30) Foreign Application Priority Data

Apr. 13, 2011   (DE) ........................ 10 2011 007 313

(51) Int. Cl.
*C12N 15/87* (2006.01)
*C12P 21/00* (2006.01)
*C12N 9/48* (2006.01)
*C12N 15/67* (2006.01)
*C12P 21/02* (2006.01)
*C12N 9/54* (2006.01)

(52) U.S. Cl.
CPC ............... *C12N 15/87* (2013.01); *C12N 9/48* (2013.01); *C12N 9/54* (2013.01); *C12N 15/67* (2013.01); *C12P 21/00* (2013.01); *C12P 21/02* (2013.01)

(58) Field of Classification Search
None
See application file for complete search history.

(56) References Cited

U.S. PATENT DOCUMENTS

2008/0199443 A1    8/2008  Moos et al.

FOREIGN PATENT DOCUMENTS

| EP | 1 873 251 A1 | 1/2008 |
|----|---|---|
| WO | WO-89/06279 A1 | 7/1989 |
| WO | WO-91/02792 A1 | 3/1991 |
| WO | WO-03/062381 A2 | 7/2003 |
| WO | WO-2004/085649 A1 | 10/2004 |
| WO | WO-2009/094084 A1 | 7/2009 |

OTHER PUBLICATIONS

Gordon et al. (Int. J. Sys. Bacteriol., 27(3):256-262, 1977).*
Goddette, D. W., et al., "The Crystal Structure of the *Bacillus lentus* Alkaline Protease, Subtilisin BL, at 1 4 Å Resolution," *Journal of Molecular Biology*. 1992, vol. 228, No., pp. 580-595.
International Search Report in international application No. PCT/EP2012/056262, dated Jun. 6, 2012.

* cited by examiner

*Primary Examiner* — Nancy Treptow
(74) *Attorney, Agent, or Firm* — Marshall, Gerstein & Borun LLP (57) ABSTRACT

The aim is to increase the protein product yield in microbial fermentation. This is achieved by a method which introduces into a microorganism not only a first expression construct which encodes the protein, but also a second expression construct which encodes an auxiliary protease which differs from the protein, is proteolytically active and which comprises an amino acid sequence which is at least 50% identical to the amino acid sequence indicated in SEQ ID NO. 1.

13 Claims, 4 Drawing Sheets

Wild type:

ΔaprE::tet:

ΔaprE::auxiliary protease:

SEQUENCE LISTING

<160> NUMBER OF SEQ ID NOS: 12

<210> SEQ ID NO 1
<211> LENGTH: 269
<212> TYPE: PRT
<213> ORGANISM: Bacillus sp.

<400> SEQUENCE: 1

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
                35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Met Ala Pro Gly Val Asn Ile Gln Ser Thr Tyr Pro Gly Ser Thr Tyr
            195                 200                 205

Ala Ser Asp Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 2
<211> LENGTH: 274
<212> TYPE: PRT
<213> ORGANISM: Bacillus sp.

<400> SEQUENCE: 2

Ala Gln Thr Val Pro Tyr Gly Ile Pro Leu Ile Lys Ala Asp Lys Val
 1               5                  10                  15

Gln Ala Gln Gly Phe Lys Gly Ala Asn Val Lys Val Ala Val Leu Asp
                 20                  25                  30

Thr Gly Ile Gln Ala Ser His Pro Asp Leu Asn Val Val Gly Gly Ala
             35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
 65                  70                  75                  80

Leu Gly Val Ala Pro Ser Val Ser Leu Tyr Ala Val Lys Val Leu Asn
                 85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
            115                 120                 125

Ser Gly Ser Thr Ala Met Lys Gln Ala Val Asp Asn Ala Tyr Ala Arg
130                 135                 140

Gly Val Val Val Val Ala Ala Ala Gly Asn Ser Gly Ser Ser Gly Asn
145                 150                 155                 160

-continued

```
Thr Asn Thr Ile Gly Tyr Pro Ala Lys Tyr Asp Ser Val Ile Ala Val
                165                 170                 175
Gly Ala Val Asp Ser Asn Ser Asn Arg Ala Ser Phe Ser Ser Val Gly
            180                 185                 190
Ala Glu Leu Glu Val Met Ala Pro Gly Ala Gly Val Tyr Ser Thr Tyr
        195                 200                 205
Pro Thr Asn Thr Tyr Ala Thr Leu Asn Gly Thr Ser Met Ala Ser Pro
    210                 215                 220
His Val Ala Gly Ala Ala Ala Leu Ile Leu Ser Lys His Pro Asn Leu
225                 230                 235                 240
Ser Ala Ser Gln Val Arg Asn Arg Leu Ser Ser Thr Ala Thr Tyr Leu
                245                 250                 255
Gly Ser Ser Phe Tyr Tyr Gly Lys Gly Leu Ile Asn Val Glu Ala Ala
            260                 265                 270
Ala Gln
```

<210> SEQ ID NO 3
<211> LENGTH: 29
<212> TYPE: DNA
<213> ORGANISM: Artificial
<220> FEATURE:
<223> OTHER INFORMATION: Primer aprE1

<400> SEQUENCE: 3
aaactgcagc gtaccggctc cttgaaagg                               29

<210> SEQ ID NO 4
<211> LENGTH: 50
<212> TYPE: DNA
<213> ORGANISM: Artificial
<220> FEATURE:
<223> OTHER INFORMATION: Primer aprE2

<400> SEQUENCE: 4
gagaagacta agcttcccga ggatcccgaa tgacaggaga ttgctccatc          50

<210> SEQ ID NO 5
<211> LENGTH: 63
<212> TYPE: DNA
<213> ORGANISM: Artificial
<220> FEATURE:
<223> OTHER INFORMATION: Primer aprE3

<400> SEQUENCE: 5
ttcgggatcc tcgggaagct tagtcttctc attctgatga aggttgttca atattttgaa  60
tcc                                                               63

<210> SEQ ID NO 6
<211> LENGTH: 30
<212> TYPE: DNA
<213> ORGANISM: Artificial
<220> FEATURE:
<223> OTHER INFORMATION: Primer aprE4

<400> SEQUENCE: 6
aaatctagat agacctcgaa gaggagaagc                              30

<210> SEQ ID NO 7
<211> LENGTH: 32
<212> TYPE: DNA
<213> ORGANISM: Artificial

```
<220> FEATURE:
<223> OTHER INFORMATION: Primer tet5

<400> SEQUENCE: 7
gcggatccaa acgggccata ttgttgtata ag                                 32

<210> SEQ ID NO 8
<211> LENGTH: 35
<212> TYPE: DNA
<213> ORGANISM: Artificial
<220> FEATURE:
<223> OTHER INFORMATION: Primer tet6

<400> SEQUENCE: 8
ccaagcttct ctcgtatctt ttattcagca atcgc                              35

<210> SEQ ID NO 9
<211> LENGTH: 50
<212> TYPE: DNA
<213> ORGANISM: Artificial
<220> FEATURE:
<223> OTHER INFORMATION: Primer aprE7

<400> SEQUENCE: 9
cgaaagtatg aatagaccgc ttcagcctgg cagggaaaga ggtcccgagg              50

<210> SEQ ID NO 10
<211> LENGTH: 50
<212> TYPE: DNA
<213> ORGANISM: Artificial
<220> FEATURE:
<223> OTHER INFORMATION: Primer aprE8

<400> SEQUENCE: 10
ctgccgctca ataacatatt ctaacaaata gcatatagaa aaagctagtg              50

<210> SEQ ID NO 11
<211> LENGTH: 50
<212> TYPE: DNA
<213> ORGANISM: Artificial
<220> FEATURE:
<223> OTHER INFORMATION: Primer ziel9

<400> SEQUENCE: 11
ctgccaggct gaagcggtct attcatactt tcgaactgaa cattttttcta             50

<210> SEQ ID NO 12
<211> LENGTH: 50
<212> TYPE: DNA
<213> ORGANISM: Artificial
<220> FEATURE:
<223> OTHER INFORMATION: Primer ziel10

<400> SEQUENCE: 12
atttgttaga atatgttatt gatcggcagc ttcgacattg atcagacctt              50
```

EXPRESSION METHOD

CROSS-REFERENCE TO RELATED APPLICATIONS

This is the U.S. national phase of International Application No. PCT/EP2012/056262, filed Apr. 5, 2012, which claims the benefit of German patent application No. 10 2011 007 313.2, filed Apr. 13, 2011.

The invention is in the field of biotechnology, more particularly microbial protein synthesis. The invention relates in particular to a method for preparing proteins by means of genetically modified microorganisms and additionally proposes microorganisms which are used in such methods. The invention further relates to uses of such microorganisms for protein preparation.

Microorganisms can be used for the preparation of materials of value. Materials of value are, for example, low-molecular-weight compounds, for instance food supplements or pharmaceutically effective compounds, or proteins, for which there is in turn a large industrial area of application owing to the diversity of proteins. Firstly, the metabolic properties of the microorganisms in question are exploited and/or modified in order to prepare the materials of value; secondly, microorganisms expressing the genes of the proteins of interest are preferably used.

For industrial-scale biotechnological production, the microorganisms in question are cultured in fermenters which are adapted accordingly to the metabolic properties of the microorganisms. During the culture, the microorganisms metabolize the supplied substrate and form the desired product, which, after the end of the fermentation, is usually separated from the production organisms and is purified and/or concentrated from the fermenter slurry and/or the fermentation medium. In the fermentative production of proteins, complex protein-rich raw materials as substrate are typically used in addition to a carbon source (typically glucose). The protein production thus corresponds to a biotransformation of substrate protein to the target protein. This requires the complete hydrolysis of the substrate protein into the individual amino acids, which are then available for biosynthesis of the target protein.

For the fermentation of microorganisms, there is consequently a comprehensive prior art, which stretches from the optimization of the strains in question, for example with respect to the rate of formation and nutrient utilization, through the technical design of the fermenters to the obtainment of the materials of value from the microorganisms in question and/or the fermentation medium.

Usually, very high product yields are desirable in microbial fermentation. For example, the international patent application WO 91/02792 discloses the improved fermentative production of an alkaline protease from *Bacillus lentus* in an optimized *Bacillus licheniformis* strain under the control of gene regulatory sequences from *Bacillus licheniformis*, more particularly the *Bacillus licheniformis* promoter.

The publications from Wu et al. (J. Bacteriol. 173(16), 4952-8 (1991); Appl. Environ. Microbiol. 68(7), 3261-9 (2002)) propose switching off proteases expressed endogenously by the microorganism in order to increase the yield of target protein. This is intended to prevent proteolytic degradation of the target protein and to focus the synthesis capacity of the microorganisms on the desired product.

There continues to be a large demand for microbial fermentation methods which allow a high product yield. It has now been found that, surprisingly and in contrast to the aforementioned publications, specifically the additional expression of a particular auxiliary protease is advantageous for the product yield.

It is an object of the present invention to increase the product yield, especially of a protein, in microbial fermentation.

The invention provides a method for preparing a protein by means of a microorganism comprising the method steps of (a) introducing into a microorganism a first expression construct which encodes the protein;

(b) introducing into the microorganism a second expression construct which encodes an auxiliary protease which differs from the protein and which comprises an amino acid sequence which is at least 50% identical to the amino acid sequence indicated in SEQ ID NO. 1, wherein the auxiliary protease has proteolytic activity;

(c) expressing the protein and the auxiliary protease in the microorganism.

A method according to the invention optionally further comprises the further method step of (d) culturing the microorganism.

In preferred embodiments according to the invention, a method according to the invention is consequently a fermentation method.

The introduction and expression of the auxiliary protease in/into the microorganism does not, unexpectedly, result in the protein product yield (target protein) decreasing, for example owing to the proteolytic activity of the expressed auxiliary protease, which might degrade synthesized target protein. On the contrary, the expression of the auxiliary protease causes the protein product yield to increase. In preferred embodiments of the invention, the auxiliary protease is involved in the hydrolysis of substrate protein and brings about, preferably together with further, chromosome-encoded proteases (=background proteases) of the microorganism, an improved digestion of the substrate protein, so that more of the required precursor molecules, more particularly amino acids, per unit time are available for the synthesis of the target protein in the production process. In such embodiments according to the invention, the substrate specificity of the background proteases and the substrate specificity of the auxiliary protease therefore complement each other advantageously with respect to the substrate digestion by the microorganism.

In this regard, it is not necessary in further preferred embodiments of the invention for the auxiliary protease to possess a significant proportion of the fermentation product. The auxiliary protease has, in this regard, a beneficial effect on the expression of the protein and, consequently, on the protein product yield, but its proportion in the fermentation product is preferably small or not even ascertainable. Preferably, its proportion in the fermentation product is less than 25% and, with increasing preference, less than 20% by weight, 15% by weight, 10% by weight, 8% by weight, 7% by weight, 6% by weight, 5% by weight, 2.5% by weight, 2% by weight, 1.5% by weight, 1% by weight, 0.5% by weight, 0.1% by weight and 0.05% by weight. The fermentation product is, in this regard, that composition in which the protein is present after a method according to the invention has been carried out, the microorganism has been cultured in a culture medium and, optionally, the microorganism has been disrupted in order to release the protein therefrom, if the protein has not been secreted by said microorganism. Preferably, the microorganisms or their fragments have been separated from the fermentation product.

In a preferred embodiment, the method according to the invention is consequently a method for increasing the expression of a protein in a microorganism. There is increased expression of the protein when a method according to the invention yields a larger amount of protein compared to a similar method which differs from a method according to the invention merely in the omission of the method step b), with the result that no auxiliary protease is consequently expressed in the microorganism in method step c). The two methods for comparison are, in this regard, carried out under the same conditions, for the same duration, and with microorganisms which merely differ through the presence or absence of the auxiliary protease.

An expression construct is a nucleic acid sequence which enables the protein or the auxiliary protease to be expressed in the microorganism. It comprises the genetic information, i.e., that nucleic acid sequence (gene) which encodes the protein or the auxiliary protease. The expression of a nucleic acid sequence is its rendering into the gene product(s) encoded by said sequence, i.e., into a polypeptide (protein) or into multiple polypeptides (proteins). The terms polypeptide and protein are used synonymously in the present application. For the purposes of the present invention, expression consequently means the biosynthesis of ribonucleic acid (RNA) and proteins from the genetic information. Generally, the expression comprises the transcription, i.e., the synthesis of a messenger ribonucleic acid (mRNA) on the basis of the DNA (deoxyribonucleic acid) sequence of the gene, and the translation of the mRNA into the corresponding polypeptide chain, which may additionally be modified posttranslationally. The expression of a protein consequently describes the biosynthesis thereof from the genetic information which is present according to the invention in the microorganism.

An expression construct further comprises at least one nucleic acid sequence, preferably DNA, having a control function for the expression of the nucleic acid sequence encoding the protein or the auxiliary protease (known as the gene regulatory sequence). A gene regulatory sequence is, in this case, any nucleic acid sequence which, through its presence in the particular microorganism, affects, preferably increases, the transcription rate of that nucleic acid sequence which encodes the protein or the auxiliary protease. Preferably, it is a promoter sequence, since such a sequence is essential for the expression of a nucleic acid sequence. However, an expression construct according to the invention can also comprise yet further gene regulatory sequences, for example one or more enhancer sequences. An expression construct for the purposes of the invention consequently comprises at least one functional unit composed of gene and promoter. It can, but need not necessarily, be present as a physical entity.

The presence of at least one promoter is essential for an expression construct according to the invention. A promoter is therefore understood to mean a DNA sequence which allows the regulated expression of a gene. A promoter sequence is naturally a component of a gene and is often situated at the 5' end thereof and thus before the RNA-coding region. Preferably, the promoter sequence in an expression construct according to the invention is situated 5' upstream of the nucleic acid sequence encoding the protein or the auxiliary protease. The most important property of a promoter is the specific interaction with at least one DNA-binding protein or polypeptide which mediates the start of the transcription of the gene by means of an RNA polymerase and is referred to as a transcription factor. Multiple transcription factors and/or further proteins are frequently involved at the start of the transcription by means of an RNA polymerase. A promoter is therefore preferably a DNA sequence having promoter activity, i.e., a DNA sequence to which at least one transcription factor binds at least transiently in order to initiate the transcription of a gene. The strength of a promoter is measurable via the transcription rate of the expressed gene, i.e., via the number of RNA molecules, more particularly mRNA molecules, generated per unit time. A promoter of an expression construct according to the invention can be an endogenous promoter of the microorganism. Such a promoter sequence is consequently naturally present in the microorganism. Alternatively, a promoter of an expression construct according to the invention can also have been introduced into the microorganism in a recombinant manner. The same also applies to all further gene regulatory sequences which an expression construct according to the invention may have.

The first expression construct encodes a protein. It consequently comprises a nucleic acid sequence encoding said protein. For this purpose, any desired nucleic acid sequence which can be translated into a protein is usable in principle. In this case, it is that protein which is to be prepared using a method according to the invention (target protein). Preferably, it is an enzyme, more preferably an enzyme as described hereinbelow.

The second expression construct encodes the auxiliary protease. The auxiliary protease differs from the protein, i.e., the auxiliary protease and the protein have different amino acid sequences. The auxiliary protease comprises an amino acid sequence which is identical to the amino acid sequence indicated in SEQ ID NO. 1 to an extent of at least 50% and, with increasing preference, to an extent of at least 55%, 60%, 65%, 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98%, 99% and very particularly preferably to an extent of 100%. Particularly preferably, the auxiliary protease has an amino acid sequence which is at least 50% identical to the amino acid sequence indicated in SEQ ID NO. 1 and is identical, with increasing preference, to an extent of at least 55%, 60%, 65%, 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98%, 99% and very particularly preferably to an extent of 100%.

The identity of nucleic acid or amino acid sequences is determined by a sequence comparison. Such a comparison is achieved by assigning similar successions in the nucleotide sequences or amino acid sequences to one another. Said sequence comparison is preferably carried out on the basis of the BLAST algorithm, which is established in the prior art and commonly used (cf. for example Altschul, S. F., Gish, W., Miller, W., Myers, E. W. & Lipman, D. J. (1990) "Basic local alignment search tool." J. Mol. Biol. 215: 403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, pages 3389-3402), and occurs principally by assigning similar successions of nucleotides or amino acids in the nucleic acid or amino acid sequences to one another. A tabular assignment of the positions in question is referred to as an alignment. A further algorithm available in the prior art is the FASTA algorithm. Sequence comparisons (alignments), more particularly multiple sequence comparisons, are usually created using computer programs. Frequently used are, for example, the Clustal series (cf. for example Chema et al. (2003): Multiple sequence alignment with the Clustal series of programs. Nucleic Acid Research 31, 3497-3500), T-Coffee (cf. for example Notredame et al. (2000): T-Coffee: A novel method for multiple sequence alignments. J. Mol. Biol. 302, 205-217) or programs based on said programs or algorithms. For the purposes of the present invention, sequence comparisons and alignments are preferably created using the computer program Vector NTI® Suite 10.3 (Invitrogen Corporation, 1600 Faraday Avenue, Carlsbad, Calif., USA) using the predefined standard (default) parameters.

Such a comparison makes it possible to reveal the similarity of the compared sequences to one another. It is usually reported in percent identity, i.e., the proportion of identical nucleotides or amino acid residues on the same positions or positions corresponding to one another in an alignment. The broadened term of homology takes conserved amino acid substitutions into consideration in the case of amino acid sequences, i.e., amino acids having similar properties, because they usually exercise similar activities or functions within the protein. Therefore, the similarity of the compared sequences can also be reported as percent homology or percent similarity. Identity and/or homology values can be reported across entire polypeptides or genes or only across particular regions. Homologous or identical regions of different nucleic acid or amino acid sequences are therefore defined by congruities in the sequences. They often have the same or similar functions. They can be small and comprise only a few nucleotides or amino acids. Such small regions often exercise essential functions for the entire activity of the protein. It may therefore be advisable to base sequence congruities only on particular, possibly small regions. Unless otherwise indicated, identity or homology values in the present application refer, however, to the entire length of the various indicated nucleic acid or amino acid sequences. In the case of proteins, more particularly enzymes and, hereunder, especially proteases, the values further refer to the various mature proteins, unless otherwise indicated. Unless otherwise indicated, the sequence view is consequently always directed to the mature, completely processed protein, even if the associated gene encodes an immature form which, after translation, is further processed to the mature form.

The auxiliary protease has, furthermore, proteolytic activity. It is consequently catalytically active, i.e., it is an active enzyme. The determination of enzyme activity can in this regard—adapted to the particular enzyme type—be carried out according to conventional measures in the art. Methods for determining activity are familiar to a person skilled in the art in the field of enzyme technology and are routinely used by such a person. Methods for determining the protease activity are, for example, disclosed in Tenside, volume 7 (1970), pages 125-132. Proteolytic activity can, furthermore, be determined via the release of the chromophore para-nitroaniline (pNA) from the substrate suc-L-Ala-L-Ala-L-Pro-L-Phe-p-nitroanilide (suc-AAPF-pNA). The protease cleaves the substrate and releases pNA. The release of the pNA causes an increase in the absorbance at 410 nm, its change in time being a measure of the enzymatic activity (cf. Del Mar et al., 1979). The measurement is carried out at a temperature of 25° C., at pH 8.6 and at a wavelength of 410 nm. The measurement time is 5 min. with a measurement interval of 20 s to 60 s. The protease activity is preferably reported in PU (protease units).

Nucleic acids and expression constructs according to the invention can be generated via methods known per se for modifying nucleic acids. Such methods are, for example, presented in relevant manuals such as the one by Fritsch, Sambrook and Maniatis, "Molecular cloning: a laboratory manual", Cold Spring Harbor Laboratory Press, New York, 1989, and familiar to a person skilled in the art in the field of biotechnology. Examples of such methods are chemical synthesis or the polymerase chain reaction (PCR), optionally in conjunction with further standard methods in molecular biology and/or chemistry or biochemistry.

The present invention is especially suitable for the recombinant preparation of proteins, more particularly enzymes. For this purpose, the first and the second expression construct are introduced into a microorganism, preferably by transformation. In this regard, the particular expression construct or parts thereof are preferably introduced via vectors, more particularly expression vectors. However, it is also possible for only parts of the expression construct, preferably at least the nucleic acid encoding the protein or the auxiliary protease, to be introduced into the microorganism in such a way that the completed expression construct only arises in the microorganism. This can, for example, be achieved by a vector which enables the gene for the protein and/or the gene for the auxiliary protease to be introduced in the host cell into an already existing genetic element such as the chromosome, the chromosomal DNA or other vectors, and so, for example, an endogenous promoter is used for the expression of the gene for the protein or of the gene for the auxiliary protease. More particularly, the gene encoding the auxiliary protease can be functionally linked in this manner to an endogenous promoter of the microorganism and then constitute the second expression construct. The term introduction consequently comprises the possibility that an expression construct is introduced, preferably transformed, in its entirety into the microorganism, but also the possibility that only part of the expression construct, particularly preferably the nucleic acid encoding the auxiliary protease, is introduced, preferably transformed, into the microorganism and the complete expression construct only arises in the microorganism. However, for the purposes of the invention, at least part of the expression construct is always introduced into the microorganism.

Vectors are known to a person skilled in the art in the field of biotechnology. Particularly when used in bacteria, they are specific plasmids, i.e., circular genetic elements. For the purposes of the present invention, the expression constructs are preferably cloned into a vector. The vectors can, for example, include those which are derived from bacterial plasmids, from viruses or from bacteriophages, or predominantly synthetic vectors or plasmids containing elements of very diverse origin. The further genetic elements present in each case enable vectors to be established in the microorganisms over multiple generations as stable units. In this respect, it is insignificant for the purposes of the invention whether they are established extrachomosomally as separate units or are integrated into a chromosome or chromosomal DNA. Which of the numerous systems is chosen depends on the individual case. Critical factors may, for example, be the achievable copy number, the selection systems available, including especially antibiotic resistances, or the culturability of the microorganisms capable of vector uptake.

Expression vectors may, furthermore, be regulatable through changes in the culture conditions, for example the cell density or the addition of particular compounds. An example of such a compound is the galactose derivative isopropyl-β-D-thiogalactopyranoside (IPTG), which is used as an activator of the bacterial lactose operon (lac operon).

In a further embodiment of the invention, a method according to the invention is distinguished by the fact that the protein is not naturally present in the microorganism and/or the auxiliary protease is not naturally present in the microorganism.

In this connection, "not naturally present" means that the protein or the auxiliary protease is not an endogenous protein or enzyme of the microorganism. The protein or the auxiliary protease consequently cannot be expressed in the microorganism by a nucleic acid sequence which is part of the chromosomal DNA of the microorganism in its wild-type form. The protein or the auxiliary protease and/or the nucleic acid sequence encoding the protein or auxiliary protease is consequently not present in the wild-type form of the microorganism and/or cannot be isolated therefrom from the wild-type form of the microorganism. Preferably, a protein not naturally present in the microorganism or an auxiliary protease not naturally present in the microorganism or the nucleic acid sequence encoding the protein or auxiliary protease has been specifically introduced into the microorganism using gene-technology methods, and so the microorganism has been enriched by the protein or the auxiliary protease or the nucleic acid sequence encoding the protein or auxiliary protease. However, a protein or the auxiliary protease can by all means be naturally present in another microorganism—relevant to the discussion is solely the microorganism used in the method.

Both the protein and the auxiliary protease may not be naturally present in the microorganism. However, in an alternative embodiment, the protein may be naturally present in the microorganism and the auxiliary protease may not be naturally present in the microorganism. In a further alternative embodiment, it is also possible for the protein not to be naturally present in the microorganism and for the auxiliary protease to be naturally present in the microorganism.

In a further embodiment of the invention, a method according to the invention is distinguished by the fact that the auxiliary protease replaces at least one chromosome-encoded protease in the microorganism. In this case, at least one existing chromosomal protease is substituted with a heterologous protease which acts as the auxiliary protease according to the invention. Preferably, the nucleic acid sequence encoding the auxiliary protease is introduced into a chromosomal nucleic acid sequence encoding a protease of the microorganism. As a result, the chromosome-encoded protease is functionally inactivated. The microorganism expresses the auxiliary protease instead of the chromosome-encoded protease. For the expression of the auxiliary protease, it is possible to use the original promoter used for the chromosome-encoded protease, and so the second expression construct comprises in this case not only the nucleic acid sequence encoding the auxiliary protease but also the promoter sequence of the chromosome-encoded protease, i.e., a natural promoter sequence of the microorganism. Alternatively, it is possible to use a promoter specifically intended for the auxiliary protease, and so the second expression construct does not comprise in this case the promoter sequence of the chromosome-encoded protease, besides the nucleic acid sequence encoding the auxiliary protease. Preferably, the second expression construct comprises in this case a nonnatural promoter sequence of the microorganism. If a promoter specifically intended for the auxiliary protease is used, it has preferably been introduced together with the nucleic acid sequence encoding the auxiliary protease into the chromosomal nucleic acid sequence encoding a protease of the microorganism. In a further alternative embodiment, for the expression of the auxiliary protease, it is possible to use both the promoter used for the chromosome-encoded protease and a promoter specifically intended for the auxiliary protease.

In a further embodiment of the invention, a method according to the invention is distinguished by the fact that the auxiliary protease is expressed in the microorganism in addition to the chromosome-encoded proteases. In this case, additional proteolytic activity is provided in the microorganism by a heterologous protease which acts as a auxiliary protease according to the invention. The second expression construct consequently comprises preferably at least the nucleic acid sequence encoding the auxiliary protease and also a promoter intended for the expression of the auxiliary protease. Preferably, the second expression construct comprises in this case a nonnatural promoter sequence of the microorganism.

In a particularly preferred embodiment, a method according to the invention is distinguished by the fact that the auxiliary protease replaces in the microorganism at least one chromosome-encoded protease which comprises an amino acid sequence which is identical to the amino acid sequence indicated in SEQ ID NO. 2 to an extent of at least 80% and, with increasing preference, to an extent of at least 81%, 82%, 83%, 84%, 85%, 86%, 87%, 88%, 89%, 90%, 91%, 92%, 93%, 94%, 95%, 96%, 97%, 98%, 99% and very particularly preferably to an extent of 100%. Particularly preferably, the chromosome-encoded protease has an amino acid sequence which is at least 80% identical to the amino acid sequence indicated in SEQ ID NO. 2 and is identical, with increasing preference, to an extent of at least 81%, 82%, 83%, 84%, 85%, 86%, 87%, 88%, 89%, 90%, 91%, 92%, 93%, 94%, 95%, 96%, 97%, 98%, 99% and very particularly preferably to an extent of 100%. Particularly preferably, such a protease is replaced in a microorganism which is a bacterium, more particularly one of the genus *Bacillus* and, hereunder, preferably in *Bacillus licheniformis*.

In a further embodiment of the invention, a method according to the invention is distinguished by the fact that the expression of the protein is enhanced by the expression of the auxiliary protease. As already explained above, the expression of the auxiliary protease in preferred embodiments according to the invention causes the protein product yield to increase. This is achieved by increased expression, i.e., increased synthesis of the protein, by the microorganism. The auxiliary protease is involved in the hydrolysis of substrate protein and brings about, optionally together with further, chromosome-encoded proteases of the microorganism, an improved digestion of substrate protein which is supplied to the microorganism during its culturing. As a result, more of the required precursor molecules, more particularly amino acids, are available for the synthesis of the protein.

This issue is determined by the transcription rate of the nucleic acid sequence encoding the protein and the translation thereof into the desired protein, i.e., by the number of proteins generated per unit time. The translation step is included in the determination of expression. Serving as comparison is a method which differs from the method according to the invention through the absence of the auxiliary protease. Such a comparison is done according to the invention in microorganisms of the same type and under the same conditions in order to ensure the comparability of the measurements.

In a further embodiment of the invention, the method is distinguished by the fact that the protein is an enzyme, more particularly a protease, amylase, cellulase, hemicellulase, mannanase, tannase, xylanase, xanthanase, xyloglucanase, β-glucosidase, pectinase, carrageenase, perhydrolase, oxidase, oxidoreductase or a lipase. Very particularly preferably, the protein is a protease. The protease to be produced (=target protease) is then simultaneously also involved in the hydrolysis of the protein substrate and can advantageously bring about a further improved digestion of substrate protein.

For example, it is possible using a method according to the invention to prepare advantageously the below-mentioned enzymes.

Among the proteases, subtilisins are preferred. Examples thereof are the subtilisins BPN' and Carlsberg, the protease PB92, the subtilisins 147 and 309, the alkaline protease from *Bacillus lentus*, subtilisin DY and the enzymes assigned to the subtilases, but no longer to the subtilisins in the narrower sense, these being thermitase, proteinase K and the proteases TW3 and TW7. Subtilisin Carlsberg is available in a further developed form under the trade name Alcalase® from Novozymes NS, Bagsværd, Denmark. The subtilisins 147 and 309 are sold by Novozymes under the trade names Esperase®, or Savinase®. Derived from the DSM 5483 protease from *Bacillus lentus* are the protease variants known by the name BLAP®. Further preferred proteases are, furthermore, the enzymes known by the name PUR for example. Further proteases are, furthermore, the enzymes available under the trade names Durazym®, Relase®, Everlase®, Nafizym®, Natelase®, Kannase® and Ovozyme® from Novozymes, the enzymes available under the trade names Purafect®, Purafect® OxP, Purafect® Prime, Excellase® and Properase® from Genencor, the enzyme available under the trade name Protosol® from Advanced Biochemicals Ltd., Thane, India, the enzyme available under the trade name Wuxi® from Wuxi Snyder Bioproducts Ltd., China, the enzymes available under the trade names Proleather® and Protease P® from Amano Pharmaceuticals Ltd., Nagoya, Japan, and the enzyme available under the name Proteinase K-16 from Kao Corp., Tokyo, Japan. Also preferred are, furthermore, the proteases from *Bacillus gibsonii* and *Bacillus pumilus*, which are disclosed in the international patent applications WO2008/086916 and WO2007/131656.

Examples of amylases are the α-amylases from *Bacillus licheniformis*, from *Bacillus amyloliquefaciens* or from *Bacillus stearothermophilus* and, in particular, also the further developments thereof improved for use in washing agents or cleaning agents. The enzyme from *Bacillus licheniformis* is available from Novozymes under the name Termamyl® and from Danisco/Genencor under the name Purastar®ST. Further-development products of this α-amylase are available from Novozymes under the trade names Duramyl® and Termamyl® ultra, from Danisco/Genencor under the name Purastar®OxAm and from Daiwa Seiko Inc., Tokyo, Japan, as Keistase®. The α-amylase of *Bacillus amyloliquefaciens* is sold by Novozymes under the name BAN®, and derived variants of the α-amylase from *Bacillus stearothermophilus* are likewise sold by Novozymes under the names BSG® and Novamyl®. Furthermore, the α-amylase from *Bacillus* sp. A 7-7 (DSM 12368) and the cyclodextrin glucanotransferase (CGTase) from *Bacillus agaradherens* (DSM 9948) should be mentioned. Similarly, fusion products of all the aforementioned molecules are usable. Moreover, the further developments of the α-amylase from *Aspergillus niger* and *A. Oryzae* are suitable, said further developments being available under the trade names Fungamyl® from Novozymes. Further advantageous commercial products are, for example, the amylase Powerase® from Danisco/Genencor and the amylases Amylase-LT®, Stainzyme® and Stainzyme Plus®, the latter from Novozymes. Variants of these enzymes obtainable by point mutations can also be prepared according to the invention. Further preferred amylases are disclosed in the published specifications WO 00/60060, WO 03/002711, WO 03/054177 and WO 07/079,938, the disclosure of which is therefore expressly incorporated herein by reference and the relevant disclosure content of which is therefore expressly incorporated into the present patent application. Amylases to be prepared according to the invention are, furthermore, preferably α-amylases.

Examples of lipases or cutinases are the lipases originally available, or further developed, from *Humicola lanuginosa* (*Thermomyces lanuginosus*), more particularly those with the amino acid substitution D96L. They are sold, for example, by Novozymes under the trade names Lipolase®, Lipolase® Ultra, LipoPrime®, Lipozyme® and Lipex®. In addition, it is possible to prepare, for example, the cutinases which have been originally isolated from *Fusarium solani pisi* and *Humicola insolens*. From Danisco/Genencor, it is possible to prepare, for example, the lipases or cutinases whose starting enzymes have been originally isolated from *Pseudomonas mendocina* and *Fusarium solanii*. Further important commercial products which should be mentioned are the preparations M1 Lipase® and Lipomax® originally sold by Gist-Brocades (now Danisco/Genencor) and the enzymes sold by Meito Sangyo KK, Japan, under the names Lipase MY-30®, Lipase OF® and Lipase PL®, and furthermore the product Lumafast® from Danisco/Genencor.

Examples of cellulases (endoglucanases, EG) comprise sequences of the fungal, endoglucanase (EG)-rich cellulase preparation, or the further developments thereof, which is supplied by Novozymes under the trade name Celluzyme®. The products Endolase® and Carezyme®, likewise available from Novozymes, are based on the 50 kD EG and the 43 kD EG, respectively, from *Humicola insolens* DSM 1800. Further commercial products of said company which can be prepared are Cellusoft®, Renozyme® and Celluclean®. It is additionally possible to prepare, for example, cellulases which are available from AB Enzymes, Finland, under the trade names Ecostone® and Biotouch® and which are at least partly based on the 20 kD EG from Melanocarpus. Further cellulases from AB Enzymes are Econase® and Ecopulp®. Further suitable cellulases are from *Bacillus* sp. CBS 670.93 and CBS 669.93, the one from *Bacillus* sp. CBS 670.93 being available from Danisco/Genencor under the trade name Puradax®. Further commercial products of Danisco/Genencor which can be prepared are "Genencor detergent cellulase L" and IndiAge® Neutra.

According to the invention, it is also possible to prepare variants of these enzymes obtainable by point mutations. Particularly preferred cellulases are *Thielavia terrestris* cellulase variants which are disclosed in the international published specification WO 98/12307, cellulases from Melanocarpus, more particularly Melanocarpus albomyces, which are disclosed in the international published specification WO 97/14804, EGIII cellulases from *Trichoderma reesei* which are disclosed in the European patent application EP 1 305 432 or variants obtainable therefrom, more particularly those which are disclosed in the European patent applications EP 1240525 and EP 1305432, and also cellulases which are disclosed in the international published specifications WO 1992006165, WO 96/29397 and WO 02/099091. The respective disclosures thereof are therefore expressly incorporated herein by reference and the relevant disclosure content thereof is therefore expressly incorporated into the present patent application.

Furthermore, it is possible to prepare further enzymes which are covered by the term hemicellulases. These include, for example, mannanases, xanthan lyases, xanthanases, pectin lyases (=pectinases), pectinesterases, pectate lyases, xyloglucanases, xylanases, pullulanases and β-glucanases. Enzymes suitable in this regard are, for example, available under the names Gamanase®, Pektinex AR® and Pectaway® from Novozymes, under the name Rohapec® B1L from AB Enzymes and under the name Pyrolase® from Diverse Corp., San Diego, Calif., USA. The β-glucanase obtained from *Bacillus subtilis* is available under the name Cereflo® from Novozymes. Hemicellulases particularly preferred according to the invention are mannanases, which are sold, for example, under the trade names Mannaway® from Novozymes or Purabrite® from Genencor.

Furthermore, it is also possible to prepare oxidoreductases, for example oxidases, oxygenases, catalases, peroxidases, such as haloperoxidases, chloroperoxidases, bromoperoxidases, lignin peroxidases, glucose peroxidases or manganese peroxidases, dioxygenases or laccases (phenol oxidases, polyphenol oxidases). Suitable commercial products which should be mentioned are Denilite® 1 and 2 from Novozymes. Further enzymes are disclosed in the international patent applications WO 98/45398, WO 2005/056782, WO 2004/058961 and WO 2005/124012.

In a further embodiment of the invention, the method is distinguished by the fact that the microorganism is a bacterium.

Bacteria are preferred microorganisms in methods according to the invention. Bacteria have short generation times and low demands in terms of culture conditions. As a result, it is possible to establish cost-effective culture methods or preparation methods. In addition, a wealth of experience is available to a person skilled in the art in the case of bacteria in fermentation technology. Both Gram-negative and Gram-positive bacteria may be suitable.

In the case of Gram-negative bacteria, for example *Escherichia coli*, a multiplicity of proteins are secreted into the periplasmic space, i.e., into the compartment between the two membranes encasing the cells. This may be advantageous for specific applications. Furthermore, it is also possible to configure Gram-negative bacteria in such a way that they eject the expressed proteins not only into the periplasmic space, but also into the medium surrounding the bacterium. By contrast, Gram-positive bacteria, for example Bacilli or microorganisms such as Actinomycetaceae or other representatives of the Actinomycetales, do not have an outer membrane, and so secreted proteins are immediately released into the medium surrounding the bacteria, generally the culture medium, from which the expressed proteins can be purified. They can be isolated directly from the medium or processed further.

A bacterium preferred according to the invention is selected from the group of the genera of *Escherichia, Klebsiella, Burkholderia, Bacillus, Staphylococcus, Corynebakterium, Arthrobacter, Streptomyces, Stenotrophomonas, Pseudomonas* and *Vibrio*. More preferably, it is one selected from the group of *Escherichia coli, Klebsiella planticola, Burkholderia glumae, Bacillus licheniformis, Bacillus lentus, Bacillus amyloliquefaciens, Bacillus subtilis, Bacillus alcalophilus, Bacillus globigii, Bacillus gibsonii, Bacillus pumilus, Staphylococcus carnosus, Corynebacterium glutamicum, Arthrobacter oxidans, Streptomyces lividans, Streptomyces coelicolor, Stenotrophomonas maltophilia* and *Vibrio metschnikovii*. Very particular preference is given to *Bacillus licheniformis*.

However, the microorganism may also be a eukaryotic cell, characterized in that it has a nucleus. In contrast to prokaryotic cells, eukaryotic cells are capable of posttranslationally modifying the protein formed. Examples thereof are fungi such as Actinomycetaceae or yeasts such as *Saccharomyces* or *Kluyveromyces*. This may be particularly advantageous when, for example, the proteins are to undergo, in conjunction with their synthesis, specific modifications, which is allowed by such systems. Modifications which eukaryotic systems carry out especially in conjunction with protein synthesis include, for example, the binding of low-molecular-weight compounds such as membrane anchors or oligosaccharides. Such oligosaccharide modifications may, for example, be desirable for lowering the allergenicity of an expressed protein. Coexpression with the enzymes naturally formed by such cells, for example cellulases or lipases, may also be advantageous. Furthermore, thermophilic fungal expression systems may, for example, be especially suitable for the expression of temperature-resistant proteins or variants.

Microorganisms to be used according to the invention can be modified with respect to their requirements in terms of culture conditions, can have other or additional selection markers, or can express yet other or additional proteins. More particularly, the microorganisms can be those which transgenically express multiple target proteins. Preferably, they secrete the protein (target protein) into the medium surrounding the microorganism.

The microorganisms for use in methods according to the invention can be cultured and fermented in a customary manner, for example in batch systems or continuous systems. In the first case, an appropriate culture medium is inoculated with the microorganisms and the protein harvested from the medium after a period to be determined experimentally. Continuous fermentation involves attaining a steady state in which, over a comparatively long period, cells partly die but also grow again and the protein formed can be removed at the same time from the medium.

Methods according to the invention are preferably fermentation methods. Fermentation methods are known per se from the prior art and constitute the actual industrial-scale production step, generally followed by an appropriate purification method for the protein prepared. All fermentation methods involving a method according to the invention for preparing a protein constitute embodiments of this inventive subject matter.

Fermentation methods characterized in that the fermentation is carried out via an intake strategy are one particular possibility. In this case, the media constituents which are consumed by the ongoing culture are additionally supplied. As a result, considerable increases both in the cell density and in the cell mass or dry mass can be attained. Furthermore, the fermentation can also be configured in such a way that unwanted metabolic products are filtered out or neutralized by addition of buffer or of counter ions appropriate in each case.

The prepared protein can be harvested from the fermentation medium. Such a fermentation method is preferred over isolation of the protein from the microorganism, i.e., product processing from the cell mass (dry mass). This can be achieved, for example, by providing suitable microorganisms of one or more suitable secretion markers or mechanisms and/or transport systems, so that the microorganisms secrete the protein into the fermentation medium. In the absence of secretion, it is alternatively possible to isolate the protein from the host cell, i.e., to purify the protein from the cell mass, for example by precipitation with ammonium sulfate or ethanol, or by chromatographic purification.

The invention further provides a microorganism obtainable by a method comprising the method steps of
(a) introducing into the microorganism a first expression construct which encodes a protein;
(b) introducing into the microorganism a second expression construct which encodes an auxiliary protease which differs from the protein and which comprises an amino acid sequence which is at least 50% identical to the amino acid sequence indicated in SEQ ID NO. 1 (=Blap S), wherein the auxiliary protease has proteolytic activity.

This is therefore all microorganisms which can be subject matter of a method according to the invention. All facts, subject matter and embodiments which are described for methods according to the invention are also applicable to this inventive subject matter. Therefore, reference is expressly made at this point to the disclosure at the corresponding point with the indication that said disclosure also applies to the microorganisms according to the invention.

Particularly preferred embodiments of microorganisms according to the invention are distinguished by the fact that
(a) the protein is not naturally present in the microorganism and/or
(b) the auxiliary protease is not naturally present in the microorganism and/or
(c) the auxiliary protease replaces at least one chromosome-encoded protease in the microorganism, or that the auxiliary protease is expressed in the microorganism in addition to the chromosome-encoded proteases, and/or
(d) the expression of the auxiliary protease enhances the expression of the protein, and/or
(e) the microorganism is a bacterium, preferably one selected from the group of the genera of *Escherichia, Klebsiella, Burkholderia, Bacillus, Staphylococcus, Corynebakterium, Arthrobacter, Streptomyces, Stenotrophomonas, Pseudomonas* and *Vibrio*, more preferably one selected from the group of *Escherichia coli, Klebsiella planticola, Burkholderia glumae, Bacillus licheniformis, Bacillus lentus, Bacillus amyloliquefaciens, Bacillus subtilis, Bacillus alcalophilus, Bacillus globigii, Bacillus gibsonii, Bacillus pumilus, Staphylococcus carnosus, Corynebacterium glutamicum, Arthrobacter oxidans, Streptomyces lividans, Streptomyces coelicolor, Stenotrophomonas maltophilia* and *Vibrio metschnikovii*. Very particular preference is given to *Bacillus licheniformis*.

Microorganisms according to the invention are used advantageously in methods according to the invention in order to prepare a protein. Consequently, the invention therefore further provides for the use of a microorganism according to the invention for preparing a protein, more particularly an enzyme.

All facts, subject matter and embodiments which are described for methods and microorganisms according to the invention are also applicable to this inventive subject matter. Therefore, reference is expressly made at this point to the disclosure at the corresponding point with the indication that said disclosure also applies to the uses according to the invention.

EXAMPLES

All the molecular biology procedural steps follow standard methods, as specified in, for example, the manual by Fritsch, Sambrook and Maniatis "Molecular cloning: a laboratory manual", Cold Spring Harbor Laboratory Press, New York, 1989, or comparable relevant works. Enzymes, kits and instruments were used according to the instructions from the respective manufacturers.

Example 1

Substitution of the gene encoding a protease according to SEQ ID NO. 2 (aprE) with a gene encoding an auxiliary protease according to SEQ ID NO. 1, in *Bacillus licheniformis*.

The following oligonucleotides were used as primers (specified in the 5'→3' orientation):

```
aprE1
                                         (SEQ ID NO. 3)
AAACTGCAGCGTACCGGCTCCTTGAAAGG aprE2
                                         (SEQ ID NO. 4)
GAGAAGACTAAGCTTCCCGAGGATCCCGAATGACAGGAGATTGCTCCATC aprE3
                                         (SEQ ID NO. 5)
TTCGGGATCCTCGGGAAGCTTAGTCTTCTCATTCTGATGAAGGTTG

TTCAATATTTTGA ATCC aprE4
                                         (SEQ ID NO. 6)
AAATCTAGATAGACCTCGAAGAGGAGAAGC tet5
                                         (SEQ ID NO. 7)
GCGGATCCAAACGGGCCATATTGTTGTATAAG tet6
                                         (SEQ ID NO. 8)
CCAAGCTTCTCTCGTATCTTTTATTCAGCAATCGC aprE7
                                         (SEQ ID NO. 9)
CGAAAGTATGAATAGACCGCTTCAGCCTGGCAGGGAAAGAGGTCC

CGAGG aprE8
                                        (SEQ ID NO. 10)
CTGCCGCTCAATAACATATTCTAACAAATAGCATATAGAAAAAGCTA

GTG ziel9
                                        (SEQ ID NO. 11)
CTGCCAGGCTGAAGCGGTCTATTCATACTTTCGAACTGAACATTTTT

CTA ziel10
                                        (SEQ ID NO. 12)
ATTTGTTAGAATATGTTATTGATCGGCAGCTTCGACATTGATCAGAC

CTT
```

Figure 1:
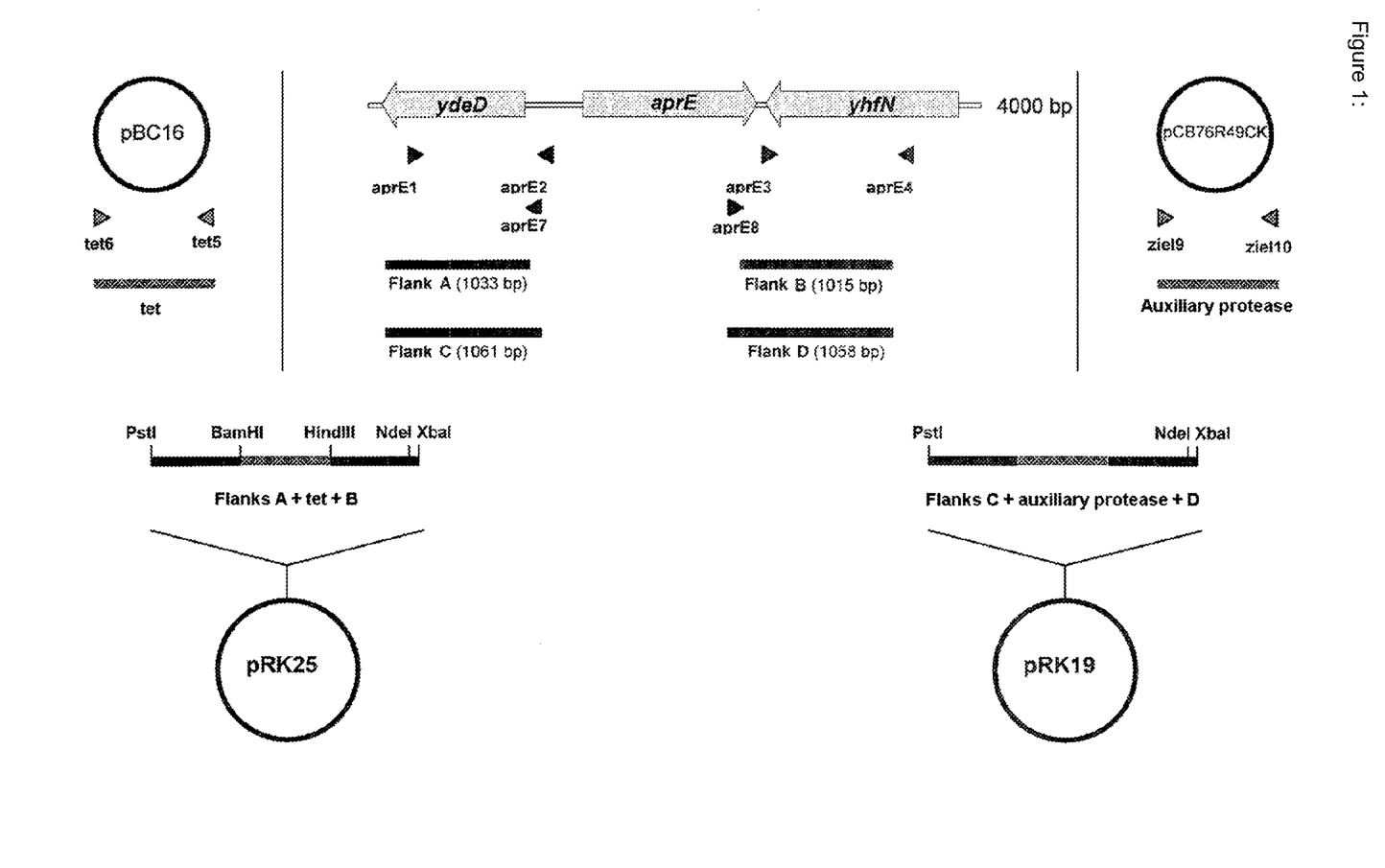
FIG. 1: Diagram showing the construction of the vectors pRK25 and pRK19 for the chromosomal substitution of the gene encoding a protease according to SEQ ID NO. 2 (aprE) with the tetracycline resistance gene tet and the gene encoding an auxiliary protease according to SEQ ID NO. 1, respectively. Arrows indicate the reading frames of the genes ydeD, aprE and yhfN, ▶ indicate primers, and bars indicate PCR products.
Figure 2:
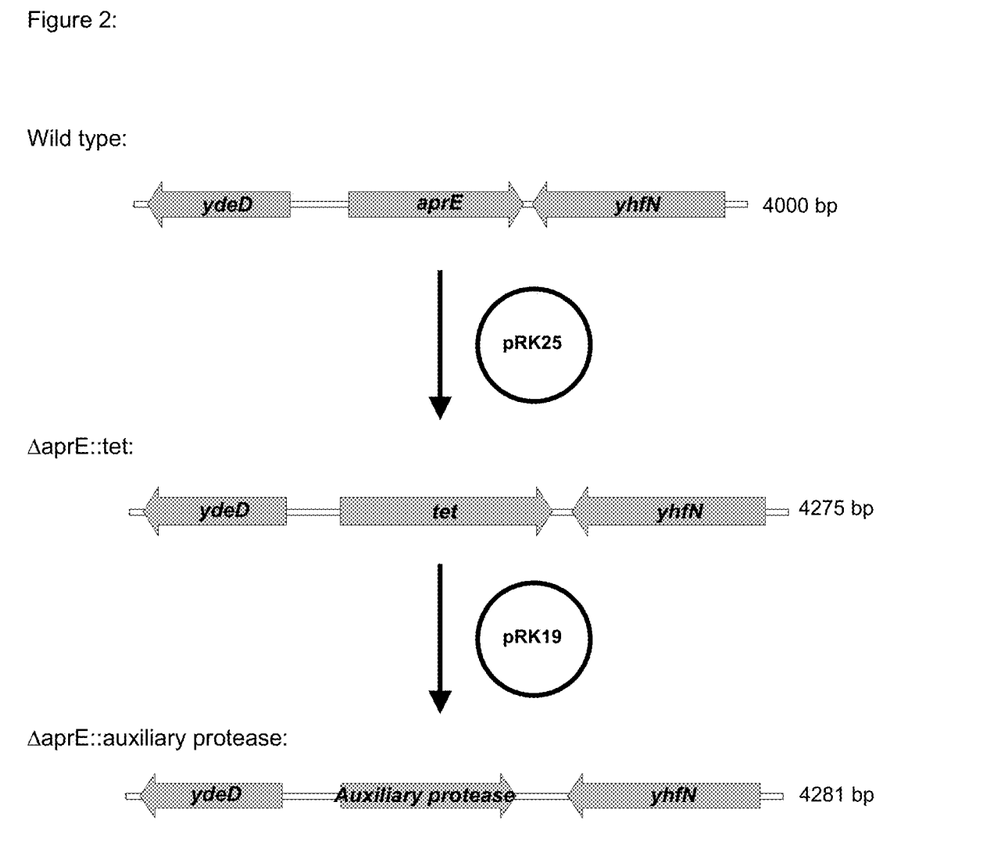
FIG. 2: Gene location of the aprE gene in Bacillus licheniformis. The figure shows the wild-type situation (top), the pRK19-mediated substitution of the aprE gene with the tetracycline resistance gene tet (middle), and the pRK25-mediated substitution of the tetracycline resistance gene tet with the gene encoding an auxiliary protease according to SEQ ID NO. 1 (bottom).

The substitution was achieved using an intermediate step in which the aprE gene was firstly substituted with the tetracycline resistance gene tet. For the substitution of the aprE gene with the tet gene, the primers aprE1 and aprE2 and the primers aprE3 and aprE4 were used to amplify sequence segments of 1033 bp and 1015 bp, respectively, upstream and downstream of the aprE gene (flanks A and B). Owing to appropriate overhangs of the primers aprE2 and aprE3, the two flanks were fused by means of fusion polymerase chain reaction (PCR) using the outer primers aprE1 and aprE4. The 2018 bp fusion PCR product was cloned into the PstI and XbaI restriction sites of the vector pE194 (Horinouchi & Weisblum, J. Bacteriol. (150), pages 804ff. (1982)). The tet gene was amplified from the plasmid pBC16 (Bernhard et al., J. Bacteriol. (133), pages 897ff., (1978)) using the primers tet5 and tet6 and cloned into the central BamHI and HindIII restriction sites of the fused aprE flanks (cf. FIG. 1). The plasmid pRK25 obtained was transformed into Bacillus licheniformis. The selection was achieved both with 5 μg/ml erythromycin and with 15 μg/ml tetracycline at 30° C. After culturing at 42° C., clones with integrated vector were identified by growth on 0.3 μg/ml erythromycin. After renewed culturing at 42° C., but without use of erythromycin, clones were obtained which were screened for tetracycline resistance and, by means of PCR, for the successful substitution of the aprE gene with the tet gene (Bacillus licheniformis ΔaprE::tet, cf. FIG. 2).

For the substitution of the tet gene with the gene encoding an auxiliary protease according to SEQ ID NO. 1, the primers aprE1 and aprE7 and the primers aprE8 and aprE4 were used to amplify sequence segments of 1061 bp and 1058 bp, respectively, upstream and downstream of the aprE gene (flanks C and D). The gene encoding an auxiliary protease according to SEQ ID NO. 1 was amplified from the plasmid pCB76R49CK using the primers ziel9 and ziel10. Owing to appropriate overhangs of the primers aprE7 and ziel9 and aprE8 and ziel10, the two flanks were fused with the auxiliary protease PCR product by means of fusion PCR using the outer primers aprE1 and aprE4. The 3704 bp fusion PCR product was cloned into the PstI and NdeI restriction sites of the vector pRK25 (cf. FIG. 1). The plasmid pRK19 obtained was transformed into Bacillus licheniformis ΔaprE::tet (see above). The selection was achieved with 5 μg/ml erythromycin at 30° C. After culturing at 42° C., clones with integrated vector were identified by growth on 0.3 μg/ml erythromycin. After renewed culturing at 42° C., but without use of antibiotic, clones were obtained which were screened by means of PCR for the successful substitution of the tet gene with the gene encoding an auxiliary protease according to SEQ ID NO. 1 (Bacillus licheniformis ΔaprE::auxiliary protease, cf. FIG. 2).

Example 2

Figure 3:
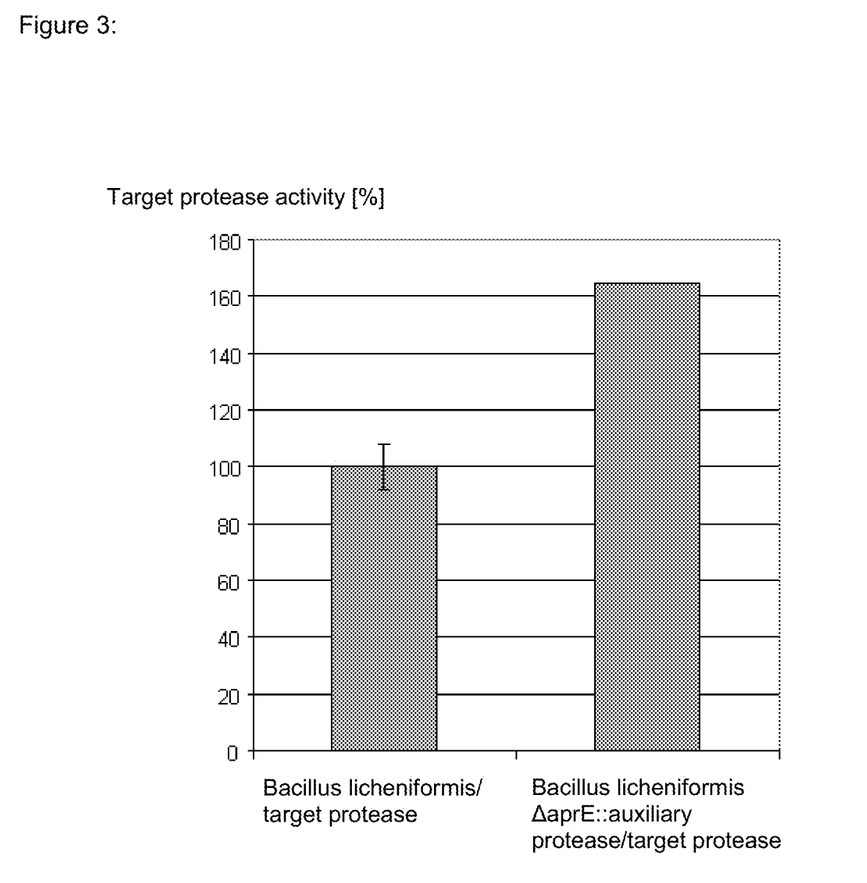
FIG. 3: Relative yields of the production strains Bacillus licheniformis/target protease and Bacillus licheniformis ΔaprE::auxiliary protease/target protease. The strains were used in a standard fermentation method for the production of the target protease.
Figure 4:
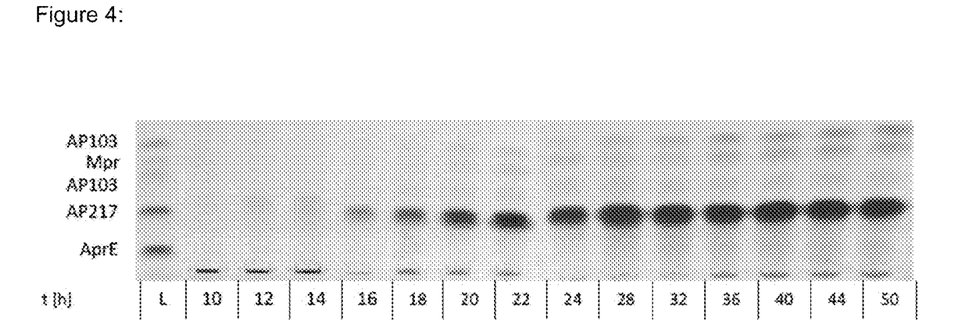
FIG. 4: Secretion analysis of the fermentation supernatant in a method according to the invention or in a microorganism according to the invention (Bacillus licheniformis ΔaprE::auxiliary protease/target protease, cf. also FIG. 3) by means of native polyacrylamide gel electrophoresis. The increased protease activity is substantially based on the activity of the target protease, since the expression and secretion thereof has been distinctly increased (t: culture time; AP103: auxiliary protease (two bands); AP217: target protease; Mpr: further size markers).

Fermentative Production of a Protease (Target Protein) Using the Production Strain Bacillus licheniformis ΔaprE::Auxiliary Protease The Bacillus licheniformis starting strain and the substitution mutant ΔaprE::auxiliary protease were transformed using a production plasmid for a protease (target protein). The resulting production strains were used in a standard fermentation method and the protease activities obtained were determined. Compared to the starting strain, the yield in the 2 liter laboratory fermenter increased by 65% (cf. FIG. 3). The measured protease activities are substantially based on the activity of the target protease, since the expression of the target protease has been distinctly increased. This was verified by secretion analysis of the fermentation supernatant of the culture of Bacillus licheniformis ΔaprE::auxiliary protease/target protease by means of native polyacrylamide gel electrophoresis (cf. FIG. 4; t is the culture time; AP103 is the auxiliary protease (two bands); AP217 is the target protease). Compared to the target protease, there is only a very low amount of auxiliary protease in the culture supernatant.

The invention claimed is:

1. A method for preparing a protein comprising
(a) introducing into a microorganism a first expression construct which encodes the protein;
(b) introducing into the microorganism a second expression construct which encodes an auxiliary protease which differs from the protein and which comprises an amino acid sequence which is at least 65% identical to the amino acid sequence indicated in SEQ ID NO. 1, wherein the auxiliary protease has proteolytic activity, and wherein the second expression construct is introduced into a chromosomal nucleic acid sequence encoding a protease of the microorganism such that the chromosome-encoded protease is functionally inactivated;
(c) expressing the protein and the auxiliary protease in the microorganism; wherein the protein is an enzyme selected from a protease, amylase, cellulase, hemicellulase, mannanase, tannase, xylanase, xanthanase, xyloglucanase, β-glucosidase, pectinase, carrageenase, perhydrolase, oxidase, oxidoreductase, or a lipase.

2. The method according to claim 1, wherein the protein is not naturally present in the microorganism and/or the auxiliary protease is not naturally present in the microorganism.

3. The method according to claim 1, wherein the chromosomal nucleic acid sequence encoding a protease into which the second expression construct is introduced encodes a protease which comprises an amino acid sequence which is at least 80% identical to the amino acid sequence indicated in SEQ ID NO. 2.

4. The method according to claim 1, wherein the expression of the protein is enhanced by the expression of the auxiliary protease.

5. The method according to claim 1 wherein the microorganism is a bacterium.

6. A microorganism obtained by a method comprising
(a) introducing into the microorganism a first expression construct which encodes a protein, wherein the protein is an enzyme selected from a protease, amylase, cellulase, hemicellulase, mannanase, tannase, xylanase, xanthanase, xyloglucanase, b-glucosidase, pectinase, carrageenase, perhydrolase, oxidase, oxidoreductase, or a lipase;
(b) introducing into the microorganism a second expression construct which encodes an auxiliary protease which differs from the protein and which comprises an amino acid sequence which is at least 65% identical to the amino acid sequence indicated in SEQ ID NO. 1, wherein the auxiliary protease has proteolytic activity, wherein the second expression construct is introduced into a chromosomal nucleic acid sequence encoding a protease of the microorganism such that the chromosome-encoded protease is functionally inactivated, and wherein the auxiliary protease is not naturally present in the microorganism.

7. The microorganism according to claim 6, wherein
(a) the protein is not naturally present in the microorganism, and/or
(b) the expression of the auxiliary protease enhances the expression of the protein, and/or
(c) the microorganism is a bacterium.

8. The method according to claim 5 wherein the bacterium is selected from the group consisting of *Escherichia, Klebsiella, Burkholderia, Bacillus, Staphylococcus, Corynebacterium, Arthrobacter, Streptomyces, Stenotrophomonas, Pseudomonas,* and *Vibrio*.

9. The method according to claim 5 wherein the bacterium is selected from the group consisting of *Escherichia coli, Klebsiella planticola, Burkholderia glumae, Bacillus licheniformis, Bacillus lentus, Bacillus amyloliquefaciens, Bacillus subtilis, Bacillus alcalophilus, Bacillus globigii, Bacillus gibsonii, Bacillus pumilus, Staphylococcus carnosus, Corynebacterium glutamicum, Arthrobacter oxidans, Streptomyces lividans, Streptomyces coelicolor, Stenotrophomonas maltophilia,* and *Vibrio metschnikovii*.

10. The microorganism according to claim 7 wherein the bacterium is selected from the group consisting of *Escherichia, Klebsiella, Burkholderia, Bacillus, Staphylococcus, Corynebacterium, Arthrobacter, Streptomyces, Stenotrophomonas, Pseudomonas,* and *Vibrio*.

11. The microorganism according to claim 7 wherein the bacterium is selected from the group consisting of *Escherichia coli, Klebsiella planticola, Burkholderia glumae, Bacillus licheniformis, Bacillus lentus, Bacillus amyloliquefaciens, Bacillus subtilis, Bacillus alcalophilus, Bacillus globigii, Bacillus gibsonii, Bacillus pumilus, Staphylococcus carnosus, Corynebacterium glutamicum, Arthrobacter oxidans, Streptomyces lividans, Streptomyces coelicolor, Stenotrophomonas maltophilia,* and *Vibrio metschnikovii*.

12. A method of preparing an enzyme using a microorganism of claim 6.

13. A method of preparing an enzyme using a microorganism of claim 7.

* * * * *

UNITED STATES PATENT AND TRADEMARK OFFICE
CERTIFICATE OF CORRECTION

PATENT NO. : 9,663,798 B2
APPLICATION NO. : 14/110724
DATED : May 30, 2017
INVENTOR(S) : Lukas Maksym et al.

It is certified that error appears in the above-identified patent and that said Letters Patent is hereby corrected as shown below:

In the Claims

At Column 23, Line 24, Claim 6, "b-glucosidase," should be -- β-glucosidase, --.

Signed and Sealed this
Twenty-fourth Day of April, 2018

Andrei Iancu
*Director of the United States Patent and Trademark Office*